(12) United States Patent
Moszner et al.

(10) Patent No.: US 7,714,034 B2
(45) Date of Patent: May 11, 2010

(54) PHOTOPOLYMERIZABLE DENTAL MATERIALS WITH BISACYLPHOSPHINE OXIDES AS INITIATORS

(75) Inventors: Norbert Moszner, Triesen (LI); Volker M. Rheinberger, Vaduz (LI); Ulrich Salz, Lindau (DE); Heinrich Gruber, Vienna (AT); Robert Liska, Vienna (AT); Beate Ganster, Vienna (AT); Gerald Ullrich, Stenbrunn (AT)

(73) Assignee: Ivoclar Vivadent AG, Schaan (LI)

( * ) Notice: Subject to any disclaimer, the term of this patent is extended or adjusted under 35 U.S.C. 154(b) by 469 days.

(21) Appl. No.: 11/385,058

(22) Filed: Mar. 21, 2006

(65) Prior Publication Data

US 2007/0027229 A1    Feb. 1, 2007

(51) Int. Cl.
  *C08F 2/50* (2006.01)
  *A61K 6/00* (2006.01)
  *A61K 6/083* (2006.01)

(52) U.S. Cl. .................. 522/64; 522/83; 522/171; 522/182; 523/115; 523/116; 523/117; 523/118

(58) Field of Classification Search ............... 522/83, 522/64, 182, 171; 523/109, 115, 116, 117, 523/118; 3/83, 64, 182
  See application file for complete search history.

(56) References Cited

U.S. PATENT DOCUMENTS

| | | | | |
|---|---|---|---|---|
| 4,259,117 A | * | 3/1981 | Yamauchi et al. | 106/35 |
| 4,368,043 A | * | 1/1983 | Yamauchi et al. | 523/118 |
| 5,472,991 A | * | 12/1995 | Schmitt et al. | 522/4 |
| 5,532,112 A | * | 7/1996 | Kohler et al. | 430/281.1 |
| 6,849,670 B2 | * | 2/2005 | Satoh et al. | 522/64 |

FOREIGN PATENT DOCUMENTS

| DE | 34 43 221 A1 | 6/1986 |
|---|---|---|
| DE | 38 01 511 C2 | 7/1989 |
| DE | 195 32 358 A1 | 3/1996 |
| DE | 197 08 294 A1 | 9/1997 |
| EP | 1 236 459 B1 | 11/2005 |
| JP | 2000-026226 A | 1/2000 |
| JP | 2000-053519 A | 2/2000 |
| WO | WO 03/019295 A1 | 3/2003 |
| WO | WO 03/068785 A | 8/2003 |

OTHER PUBLICATIONS

Richards et al., "Dental Polymeric Composites Activated with Camphorquinone Diacyl Phosphine Oxide Photoinitiators," *Polymer Reprints* 45(2):362-363 (2004).

* cited by examiner

*Primary Examiner*—Susan W Berman
(74) *Attorney, Agent, or Firm*—Nixon Peabody LLP

(57) ABSTRACT

Polymerizable dental material which contains at least one radically-polymerizable monomer and at least one bisacylphosphine oxide of the Formula I, Formula (I)

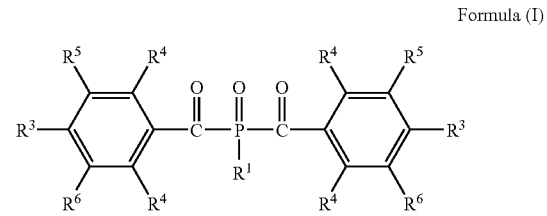

in which $R^1$ is a linear or branched $C_2$ to $C_{14}$ alkyl residue, which can be interrupted by one or more O atoms, PG-Y—$R^2$—X— or a substituted or unsubstituted, aromatic $C_6$ to $C_{14}$ radical; $R^2$ is absent or a linear or branched $C_1$ to $C_{20}$ alkylene radical, which can be interrupted by one or more O atoms; $R^3$ is H, a linear or branched $C_1$ to $C_6$ alkyl residue or PG-Y—$R^2$—X—; $R^4$ is a linear or branched $C_1$-$C_6$ alkyl or —O—$C_1$-$C_6$ alkyl residue; $R^5$ is H or PG-Y—$R^2$—X—; $R^6$ is H or PG-Y—$R^2$13 X—; PG is a polymerizable group; X is absent, O or S; Y is absent, O, S, an ester, amide or urethane group; the bisacylphosphine oxide having at least one PG-Y—$R^2$—X group and X and/or Y being absent if $R^2$ is absent.

18 Claims, No Drawings

PHOTOPOLYMERIZABLE DENTAL MATERIALS WITH BISACYLPHOSPHINE OXIDES AS INITIATORS

The invention relates to polymerizable dental materials such as adhesives, coatings, cements and composites which contain bisacylphosphine oxides as photoinitiators.

A large number of radically polymerizable dental materials, such as e.g. sealants, dentine and enamel adhesives, fixing materials and filling composites, are predominantly cured by irradiation with light. The reason for this is the easy manageability of light-curing materials. They mostly have one component, i.e. they need not be mixed before use. Furthermore they show a long processing time and then cure quickly if desired upon irradiation. They are also characterized by a good storage stability at room temperature.

For reasons of tissue compatibility and adequate curing in the case of pigmented systems, irradiation with light is generally in the wavelength range of 400 to 500 nm. One of the first photoinitiator systems used in radically polymerizable-dental materials was the combination of an α-diketone and an amine as described in GB 1 408 265. Corresponding dental compositions which contain this photoinitiator system are disclosed e.g. in U.S. Pat. Nos. 4,457,818 and 4,525,256, camphorquinone preferably being used as α-diketone. However, other diketones have also been used, such as e.g. combinations of 1-aryl-2-alkyl-1,2-ethanediones with cyclic diketones (U.S. Pat. No. 6,204,302).

Single-component photoinitiators, so-called α-splitters such as titanocenes, acylphosphonates, acylphosphine oxides or bisacrylphosphine oxides, are also used in light-curing dental materials. Titanocenes are however not particularly reactive and are preferably used in combination with amines and/or peroxides (EP 0 334 338). Acylphosphonates such as e.g. benzoyl-di(2,6-dimethylphenyl)phosphonate are also, on account of their small curing depth, preferably used in combination with a second initiator system, such as e.g. the camphorquinone/amine system (EP 0 336 417 A2).

EP 0173 567 A2 discloses dental compositions which contain acylphosphine oxides as initiators for radical polymerization, such as e.g. the 2,4,6-trimethylbenzoyl-diphenylphosphine oxide described in DE 29 09 992 A1.

EP 1 236 459 A1 describes a dental composition which contains acyl or bisacylphosphine oxides as photoinitiators. The materials contain a special mixture of filler particles which are said to endow the materials with an improved surface brightness after curing.

Dental compositions which contain a combination of acylphosphine oxide, organic peroxide, tertiary amine and aromatic sulphinic acid as initiator are disclosed in EP 0 948 955 A1. Acid monomers among others can be used as monomers.

US 2002/0035169 A1 describes an antibacterial adhesive composition in which a mixture of acylphosphine oxide and an α-diketone is preferably used as initiator system.

DE 34 43 221 A1 discloses bisacylphosphine oxides which are said to be suitable as initiators for the photopolymerization of compounds with C=C bonds.

Photopolymerizable dental compositions which can be cured in two steps are known from DE 38 01 511 A1. These masses contain a first photoinitiator component with an absorption maximum of <450 nm and a second photoinitiator component with an absorption maximum of >450 nm. Bisacylphosphine oxides are used as first photoinitiator component and α-diketones as second photoinitiator component.

DE 38 37 569 A1 relates to photopolymerizable dental compositions which contain bisacylphosphine oxides as photoinitiators for thiol-ene polymerization.

U.S. Pat. No. 5,399,770 discloses the use of alkylbisacylphosphine oxides as photoinitiators for dental materials based on ethylenically unsaturated compounds. The photoinitiators are said to be easy to prepare.

DE 195 32 358 A1 discloses the use of alkoxyphenyl-substituted bisacylphosphine oxides which are active in the range from approx. 200 to approx. 600 nm as photoinitiators for photopolymerization.

WO 03/019295 A1 discloses bathochromic mono- and bisacylphosphine oxides which are suitable as photoinitiators for olefinically unsaturated monomers.

Photoinitiator systems which comprise an α-diketone and an amine are suitable only to a limited degree for use in self-etching, self-conditioning dental materials. Such dental materials normally contain acid monomers which are able to etch the hard tooth substance, so that a preconditioning of the hard tooth substance with acid is not necessary. α-diketone/amine photoinitiator systems are however protonated by the acid monomers and thus suffer a loss of efficiency.

Although photoinitiators such as acyl and bisacylphosphine oxides which form polymerization-triggering radicals through monomolecular bond cleavage, so-called Norrish type I-cleavage, are better suited under acid conditions, they have the disadvantage that they are only little soluble in aqueous systems. Moreover, in most cases, higher initiator concentrations are required compared with α-diketone/amine photoinitiator systems so that there is the danger that, after curing of the materials, non-reacted and thus elutable photoinitiator portions are present, which is disadvantageous from a toxicological point of view. Moreover it is known of acylphosphine oxides that the carbon/phosphorus bond is easily split by nucleophilic compounds, such as e.g. water or alcohols. The photoinitiator is thereby gradually degraded, which has as a consequence a loss of activity of the initiators and thus an incomplete curing of the restoration material. This means that the dental materials lose their clinical suitability over time during storage.

Accordingly the object of the invention is to provide photoinitiators for dental materials which trigger polymerization in the visible region, are well soluble in aqueous systems and are stable in the presence of water and acids.

This object is achieved according to the invention by polymerizable dental materials which contain at least one radically polymerizable monomer and at least one bisacylphosphine oxide of the formula I

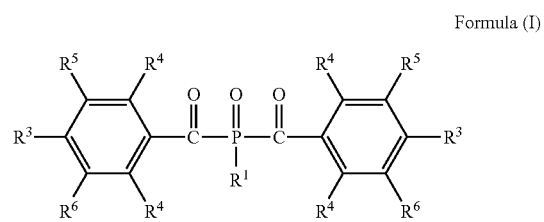

Formula (I)

in which the variables have the following meanings, independently of one another:

$R^1$ = a linear or branched $C_2$ to $C_{14}$ alkyl residue which can be interrupted by one or more O atoms, PG-Y—$R^2$—X—, a substituted or unsubstituted, aromatic $C_6$ to $C_{14}$ residue;

$R^2$ = is absent or can be a linear or branched $C_1$ to $C_{20}$ alkylene radical which can be interrupted by one or more O atoms, $R^3$=H, a linear or branched $C_1$ to $C_6$ alkyl residue or PG-Y—$R^2$—X—,
$R^4$=a linear or branched $C_1$-$C_6$ alkyl or —O—$C_1$-$C_6$ alkyl residue,
$R^5$=H or PG-Y—$R^2$—X—,
$R^6$=H or PG-Y—$R^2$—X—,
PG=a polymerizable group,
X=is absent, O or S,
Y=is absent, O, S, an ester, amide or urethane group, the bisacylphosphine oxide having at least one PG-Y—$R^2$—X group and X and/or Y being absent if $R^2$ is absent.

The detail that groups can be interrupted by oxygen atoms is to be understood to mean that oxygen atoms are inserted in the carbon chain of the groups, i.e. bound on both sides by carbon atoms. The oxygen atoms cannot thus adopt a terminal position. If several atoms are integrated into a carbon chain they must be separated from each other in each case by at least one carbon atom. Annular molecule groups are not meant by. "carbon chain". The total number of atoms integrated in the carbon chain is smaller by at least 1 than the number of carbon atoms in the chain.

The substituents optionally present in the case of $R^1$ are preferably selected from $C_1$ to $C_{15}$ alkoxy radicals which can be interrupted by one or more O atoms, PG-Y—$R^2$—X, thiomethyl, dimethylamino and/or diethylamino groups, particularly preferably from $C_1$ to $C_6$ alkoxy radicals which can be interrupted by one or more O atoms, and PG-Y—$R^2$—X—. The aromatic radicals can be substituted one or more times, preferably 1 to 2 times.

Preferred polymerizable groups are the vinyl, allyl, (meth)acryloyl and/or vinylcyclopropyl group.

Compounds of the formula (I) in which X is absent and $R^2$ is a linear or branched $C_1$ to $C_{20}$ alkylene radical which can be interrupted by one or more O atoms are preferred.

Preferred meanings of the variables, which can be selected independently of one another, are:
$R^1$ phenyl which is unsubstituted or substituted by PG-Y—$R^2$—X—;
$R^2$ —[$CH_2$]$_n$—[—O—$CH_2$—$CH_2$]$_m$— with n=1, 2, 3 or 4 and m=0, 1, 2 or 3;
$R^3$ H, $C_1$-$C_3$ alkyl or PG-Y—$R^2$—X—;
$R^4$ $C_1$-$C_3$ alkyl or —O—$C_1$-$C_3$ alkyl;
$R^5$ H or PG-Y—$R^2$—X—;
$R^6$ H or PG-Y—$R^2$—X—;
PG —$CH_2$—CH=$CH_2$ or —CH=$CH_2$;
X is absent;
Y is absent or O.

If m=0, Y is preferably O.

The bisacylphosphine oxide of the formula (I) preferably has 1 to 5, particularly preferably 1 to 3 PG-Y—$R^2$—X groups.

The functionalized bisacylphosphine oxides of the general formula (I) can be produced by multi-stage synthesis processes known bisacylphosphine oxides. For example in the first synthesis steps suitably substituted benzoyl chlorides are produded e.g. by etherification of correspondingly substituted bromobenzoic acid and subsequent conversion into the acid chloride with thionyl chloride, which in a second step are then reacted with a suitably substituted dilithium alkyl or aryl phosphine and the formed products then further oxidized with hydrogen peroxide to the bisacylphosphine oxide of the formula (I):

1st stage:

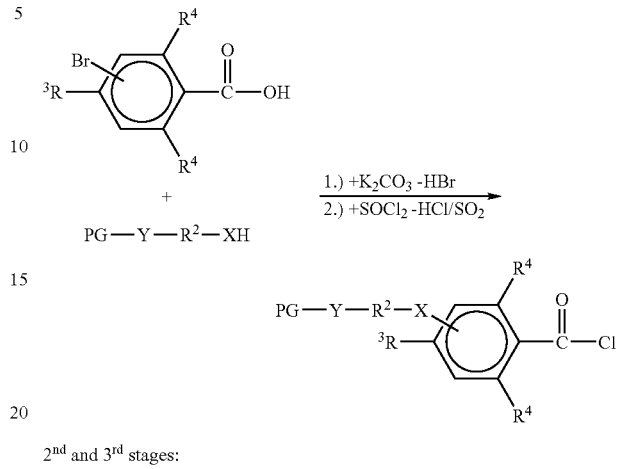

2nd and 3rd stages:

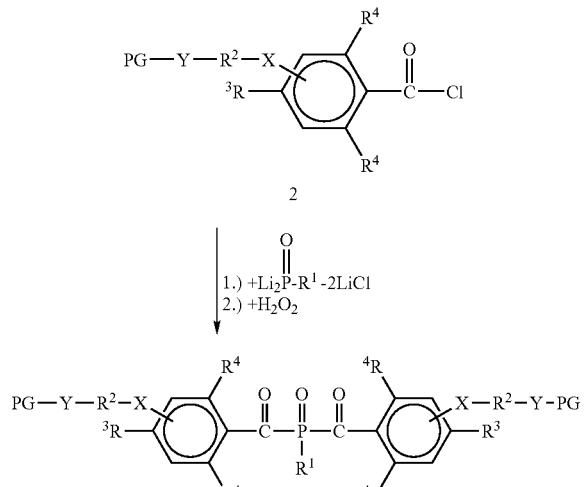

Specific Example:

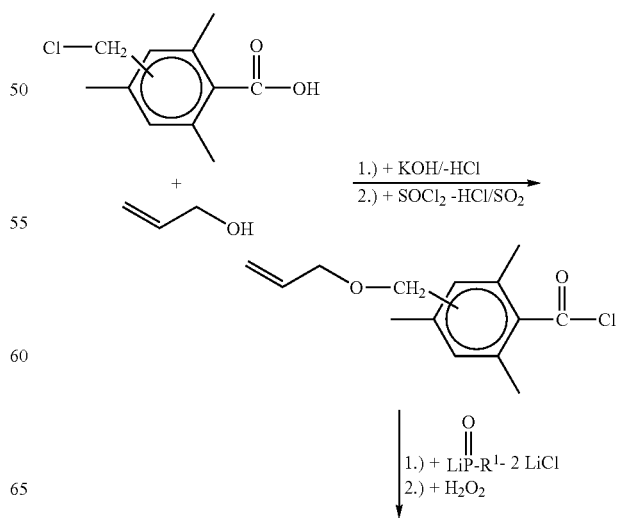

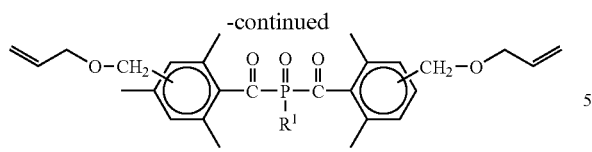
Preferred examples of the bisacylphosphine oxides according to the invention are given below:
bis-(3-allyloxymethyl-2,4,6-trimethyl-benzoyl)-phenylphosphine oxide:
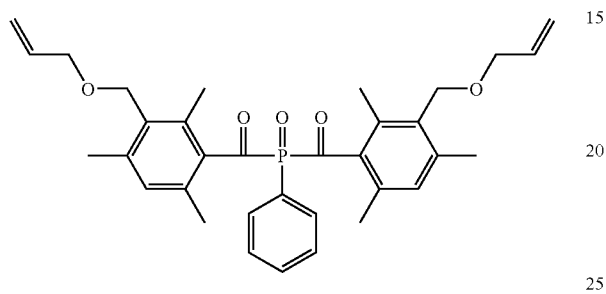
bis-[3-(2-allyloxy-ethoxymethyl)-2,4,6-trimethylbenzoyl]-phenylphosphine oxide:
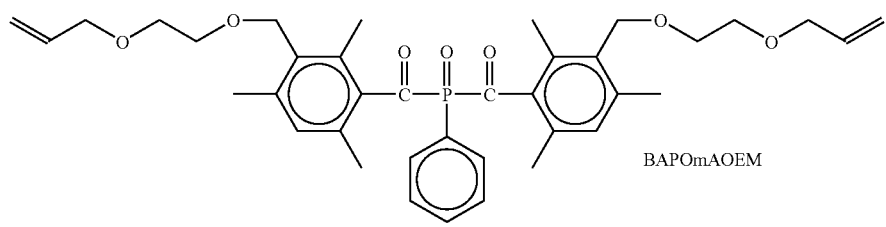
BAPOmAOEM
bis-{3-[2-(2-allyloxy-ethoxy)-ethoxymethyl]-2,4,6-trimethyl-benzoyl}-penylphosphine oxide:
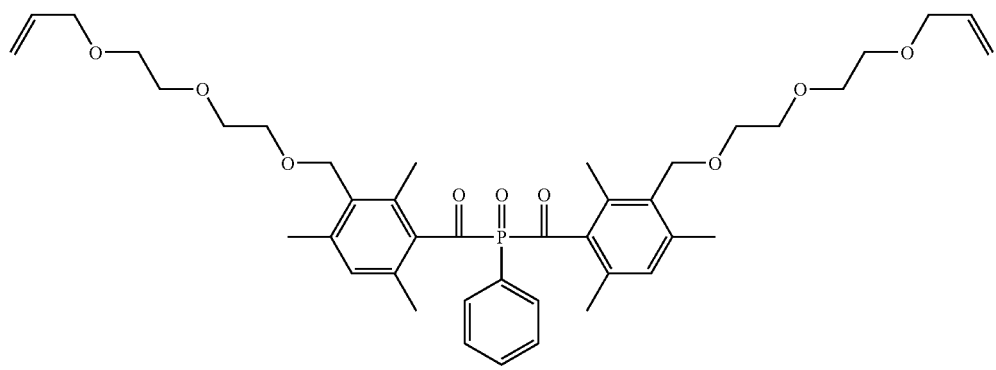

bis-(3-allyloxymethyl-2,6-dimethoxy-4-methyl-benzoyl)-phenylphosphine oxide:
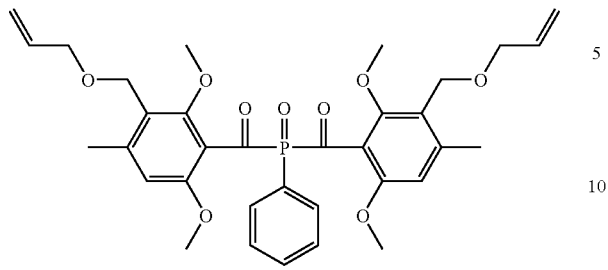
bis-{[3-(2-allyloxy-ethoxymethyl)-2,6-dimethoxy-4-methyl-benzoyl}-phenylphosphine oxide:
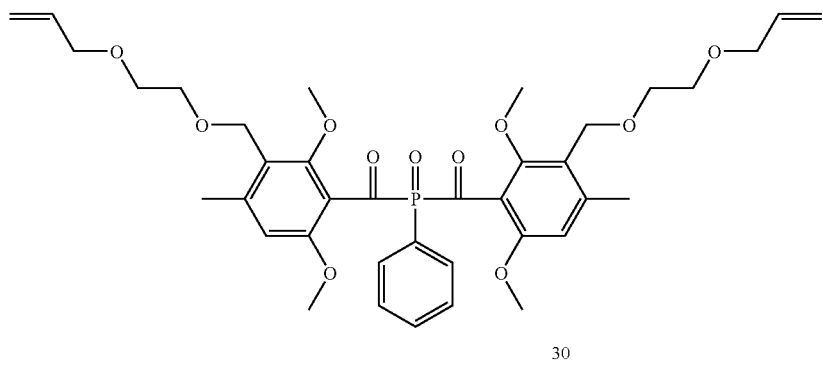
bis-{3-[2-(2-allyloxy-ethoxy)-ethoxymethyl]-2,6-dimethoxy-4-methyl-benzoyl}-phenylphosphine oxide:
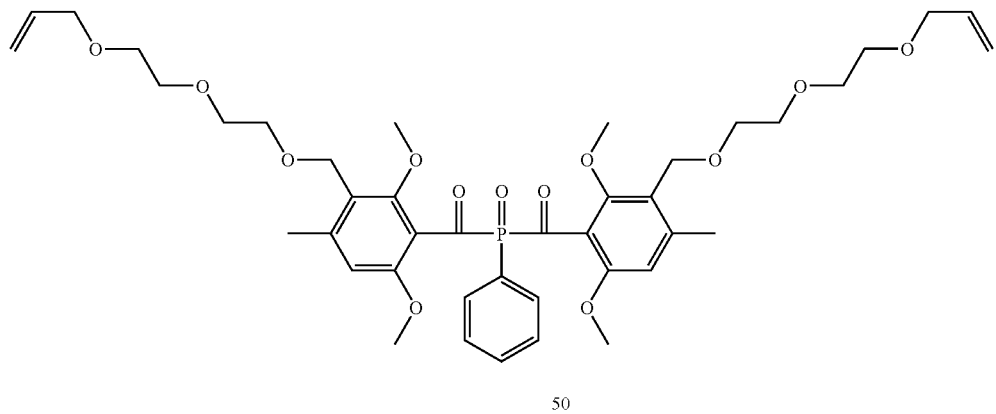
bis-{3,5-[bis-(allyloxymethyl)-2,4,6-trimethyl-benzoyl]}-phenylphosphine:
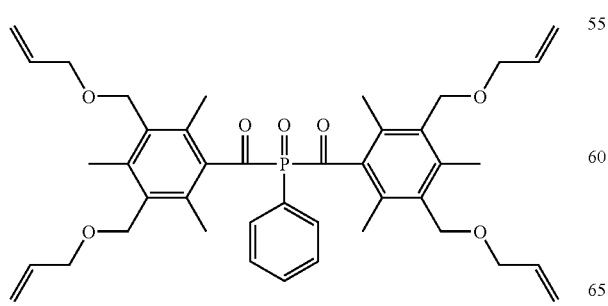

bis-{3,5-[bis-(2-allyloxy-ethoxymethyl)-2,4,6-trimethyl-benzoyl]}-phenylphosphine oxide:
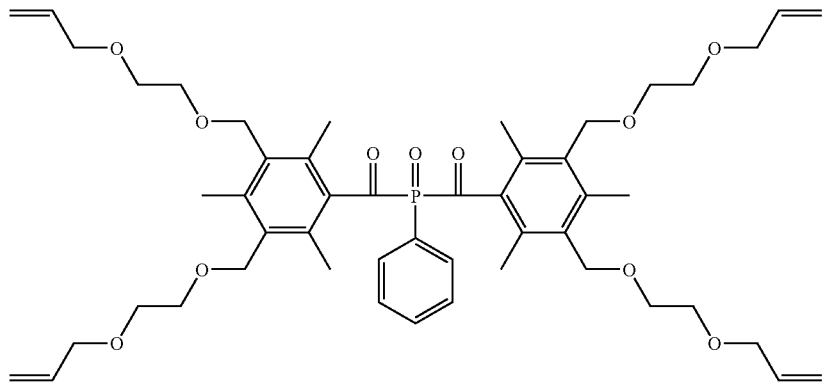
bis-{3,5-bis-[2-(2-allyloxy-ethoxy)-ethoxymethyl]-2,4,6-trimethyl-benzoyl}-phenylphosphine oxide:
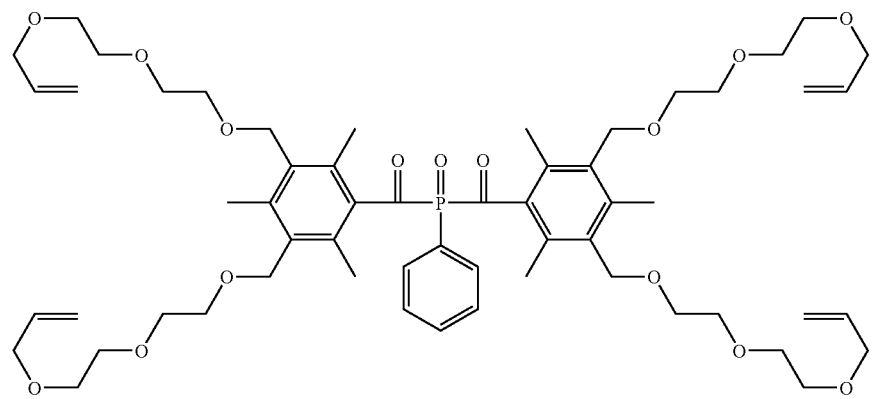
bis-{3,5-[bis-(allyloxymethyl)-2,6-dimethoxy-4-methyl-benzoyl]}-phenylphosphine:
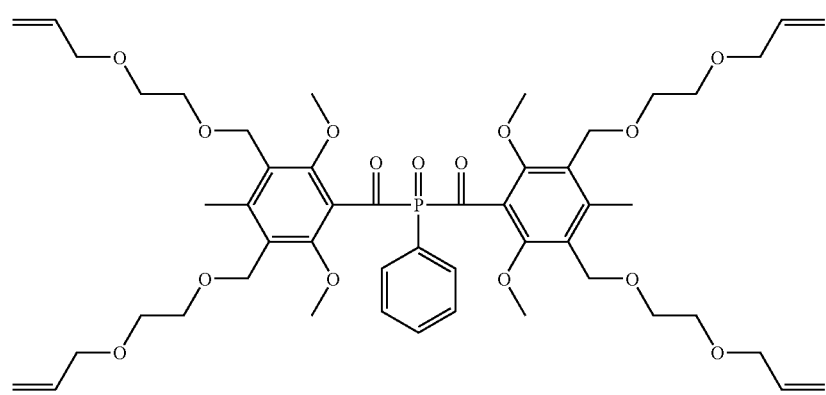

bis-{3,5-[bis-(2-allyloxy-ethoxymethyl)-2,6-dimethoxy-4-methyl-benzoyl]}-phenylphosphine oxide:
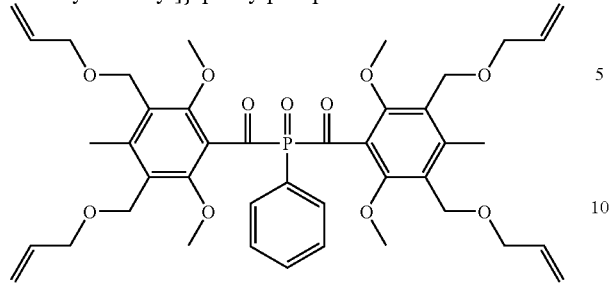
bis-{3,5-bis-[2-(2-allyloxy-ethoxy)-ethoxymethyl]-2,6-dimethoxy-4-methyl-benzoyl}-phenylphosphine oxide:
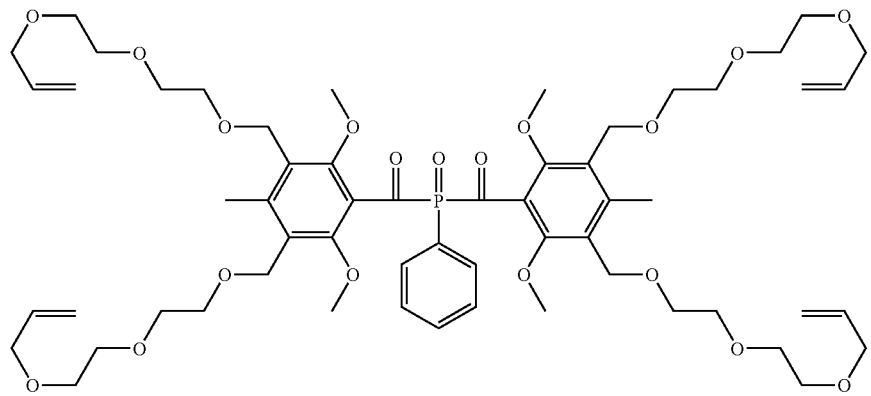
bis-[2,4,6-trimethyl-benzoyl]-{4-[2-(2-allyloxy-ethoxy)-ethoxymethyl]-phenyl}-phosphine oxide:
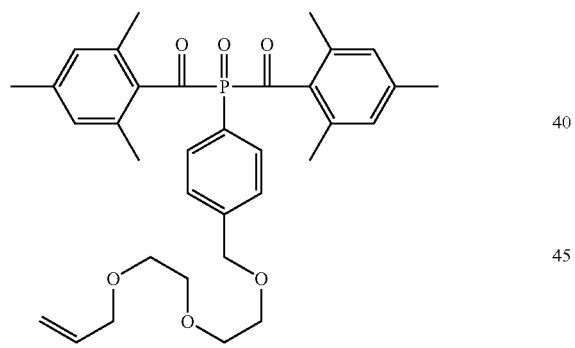
bis-[2,4,6-trimethyl-benzoyl]-[4-(2-allyloxy-ethoxymethyl)-phenyl]-phosphine oxide:
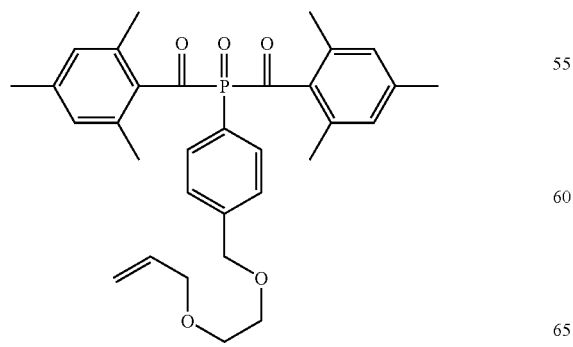

bis-[2,4,6-trimethyl-benzoyl]-[4-allyloxymethyl-phenyl]-phosphine oxide:

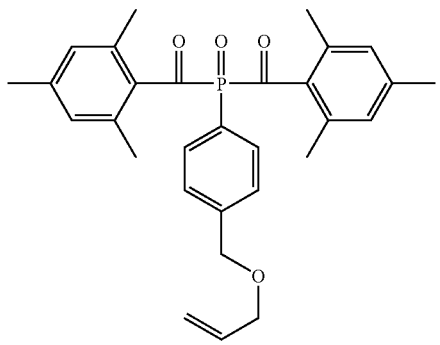

bis-[2,6-dimethoxy-benzoyl]-[4-allyloxymethyl-phenyl]-phosphine oxide:

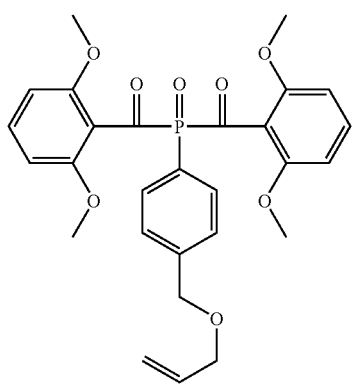

bis-[2,6-dimethoxy-benzoyl]-[4-(2-allyloxy-ethoxymethyl)-phenyl]-phosphine oxide:

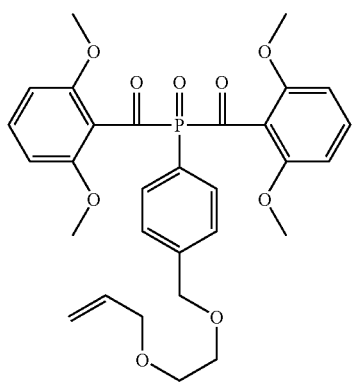

bis-[2,6-dimethoxy-benzoyl]-{4-[2-(2-allyloxy-ethoxy)-ethoxymethyl]-phenyl}-phosphine oxide:

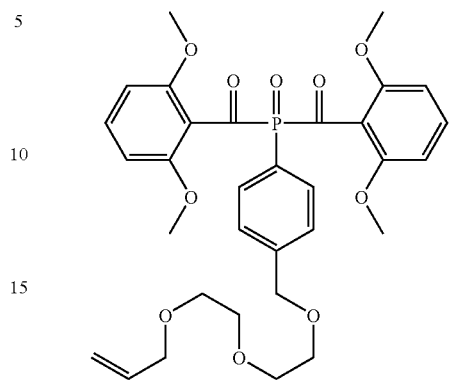

The bisacylphosphine oxides of the formula (I) absorb in the UV region and also show an absorption greater than 400 nm, so that their photolysis and radical formation can be induced by irradiation with halogen lamps customary in the dental field or also with LED lamps. The bisacylphosphine oxides of the formula (I) contain polymerizable groups and can be incorporated into polymers e.g. by copolymerization. Moreover, the bisacylphosphine oxides according to the invention are very well soluble in polar organic solvents such as acetone, ethanol, acetonitrile or tetrahydrofuran (THF) or their mixtures with water, i.e. the solubility is at least 0.01 mmol/g. It is particularly advantageous that the bisacylphosphine oxides according to the invention show a better storage stability compared with known bisacrylphosphine oxides. The compounds are characterized by a high hydrolysis stability, i.e. they are not more than 15% hydrolyzed in a mixture of $CH_3CH:H_2O$ (60:40) at 42° C. in 60 days.

The dental material according to the invention can contain mono- or multifunctional (meth)acrylates as radically polymerizable monomers. By monofunctional (meth)acryl compounds are meant compounds with one, by multifunctional (meth)acryl compounds, compounds with two or more, preferably 2 to 3, (meth)acryl groups. Multifunctional monomers have cross-linking properties.

Preferred monofunctional (meth)acrylates are commercially available monofunctional monomers such as methyl, ethyl, butyl, benzyl, furfuryl or phenyl(meth)acrylate as well as 2-hydroxyethyl or propyl(meth)acrylate.

Particularly preferred are hydrolysis-stable monomers such as hydrolysis-stable mono(meth)acrylates, e.g. mesityl methacrylate or 2-(alkoyxymethyl)acrylic acid, e.g. 2-(ethoxymethyl)acrylic acid, 2-(hydroxymethyl)acrylic acid, N-mono- or disubstituted acrylamides, such as e.g. N-ethyl acrylamide, N,N-dimethacrylamide, N-(2-hydroxyethyl)acrylamide or N-methyl-N-(2-hydroxyethyl)acrylamide, and N-monosubstituted methacrylamides, such as e.g. N-ethyl methacrylamide or N-(2-hydroxyethyl)methacrylamide and also N-vinylpyrrolidone and allyl ether. These monomers are liquid at room temperature and are therefore also suitable as diluents.

Preferred multifunctional monomers are bisphenol-A-di(meth)acrylate, bis-GMA (an addition product of methacrylic acid and bisphenol-A-diglycidylether), UDMA (an addition product of 2-hydroxyethyl methacrylate and 2,2,4-trimethyl-hexamethylene diisocyanate), di-, tri- or tetraethylene glycoldi(meth)acrylate, trimethylolpropane tri(meth)acrylate, pentaerythritol tetra(meth)acrylate, and butanediol di(meth)acrylate, 1,10-decanediol di(meth)acrylate or 1,12-dodecanediol di(meth)acrylate.

Particularly preferred are hydrolysis-stable cross-linking monomers such as e.g. urethanes from 2-(hydroxymethyl) acrylic acid and diisocyanates, such as 2,2,4-trimethylhexamethylene diisocyanate or isophorone diisocyanate, cross-linking pyrrolidones, such as e.g. 1,6-bis(3-vinyl-2-pyrrolidonyl)-hexane, or commercially available bisacrylamides such as methylene or ethylene bisacrylamide, bis-(meth)acrylamides, such as e.g. N,N'-diethyl-1,3-bis-(acrylamido)-propane, 1,3-bis-(methacrylamido)-propane, 1,4-bis-(acrylamido)-butane or 1,4-bis-(acryloyl)-piperazine which can be synthesized by reaction from the corresponding diamines with (meth)acrylic acid chloride.

The dental materials according to the invention preferably also contains at least one radically polymerizable, acid group-containing monomer. Preferred acid groups are carboxylic acid groups, phosphonic acid groups, phosphate groups and/or sulphonic acid groups, groups with more than one acid hydrogen atom can be partly esterified. Particularly preferred are monomers with phosphonic acid groups or phosphate groups. The monomers can have one or more acid groups, compounds with 1 to 2 acid groups being preferred.

Preferred polymerizable carboxylic acids are maleic acid, acrylic acid, methacrylic acid, 2-(hydroxymethyl)acrylic acid, 4-(meth)acryloyloxyethyl trimellitic acid anyhdride, 10-methacryloyloxydecyl malonic acid, N-(2-hydroxy-3-methacryloyloxypropyl)-N-phenylglycine and 4-vinylbenzoic acid.

Preferred phosphonic acid monomers are alkene phosphonic acids, vinyl phosphonic acid, 4-vinylphenyl phosphonic acid, 4-vinylbenzyl phosphonic acid, 2-methacryloyloxyethyl phosphonic acid, 2-methacrylamidoethyl phosphonic acid, 4-methacrylamido-4-methyl-pentyl-phosphonic acid, 2-[4-(dihydroxyphosphoryl)-2-oxa-butyl]-acrylic acid and 2-[2-dihydroxyphosphoryl)-ethoxymethyl]-acrylic acid-2,4,6-trimethyl-phenyl ester.

Preferred acid polymerizable phosphoric acid esters (phosphates) are 2-methacryloyloxypropylmono- and dihydrogen phosphate, 2-methacryloyloxyethylmono- and dihydrogen phosphate, 2-methacryloyloxyethyl-phenyl-hydrogenphosphate, dipentaerythritol-pentamethacryloyloxyphosphate, 10-methacryloyloxydecyl-dihydrogen phosphate, dipentaerythritolpentamethacryloyloxy phosphate, phosphoric acid mono-(1-acryloyl-piperidine-4-yl)-ester, 6-(methacrylamido)hexyldihydrogen phosphate and 1,3-bis-(N-acryloyl-N-propyl-amino)-propane-2-yl-dihydrogen phosphate.

Preferred polymerizable sulphonic acids are vinyl sulphonic acid, 4-vinylphenyl sulphonic acid or 3-(methacrylamido)propyl sulphonic acid.

Moreover, the dental materials can contain organic or inorganic particulate fillers to improve the mechanical properties or to set the viscosity. Preferred inorganic particulate fillers are amorphous spherical materials based on oxides, such as $ZrO_2$ and $TiO_2$, nanoparticulate or microfine fillers such as pyrogenic silica, nanoparticulate $Al_2O_3$, $Ta_2O_5$, $Yb_2O_3$, $ZrO_2$, Ag or $TiO_2$ or mixed oxides of $SiO_2$, $ZrO_2$ and/or $TiO_2$, or precipitated silica and minifillers, such as quartz, glass ceramic or glass powder with an average particle size of 0.01 to 1 μm and X-ray-opaque fillers such as ytterbium trifluoride or nanoparticulate barium sulphate. Particularly suitable are fillers which are surface-modified by polymerizable groups.

Moreover, the dental materials according to the invention can contain one or more further additives which are selected from stabilizers; aromatics, antimicrobial active ingredients, fluoride-ion releasing, optical brighteners, plasticizers and/or UV absorbers.

The dental materials are suitable e.g. as filling materials and particularly as coating materials, adhesives, self-adhesive and/or self-conditioning fixing cements.

The dental materials according to the invention preferably contains:

a) 0.001 to 5 wt.-%, preferably 0.01 to 3.0 wt.-% and particularly preferably 0.1 to 2.0 wt.-% bisacylphosphine oxide of the formula (I);

b) 5 to 80 wt.-%, preferably 5 to 60 wt.-% and particularly preferably 5 to 50 wt.-% mono- or multifunctional monomer;

c) 1 to 60 wt.-%, preferably 5 to 50 wt.-% and particularly preferably 5 to 45 wt.-% acid radically polymerizable monomer;

d) 0 to 80 wt.-%, preferably 0 to 60 wt.-% and particularly preferably 0 to 40 wt.-% solvent;

e) 0 to 85 wt.-% filler.

Dental materials for use as adhesive preferably contain 0 to 30 wt.-% filler and dental materials for use as cement or filling material 20 to 85 wt.-% filler.

The invention is described in more detail in the following with the help of examples.

EXAMPLES

Example 1

Synthesis of bis-{3-[2-(2-allyloxy-ethoxymethyl]-2,4,6-trimethylbenzoyl}-phenylphosphine oxide (BAPOmAOEM)

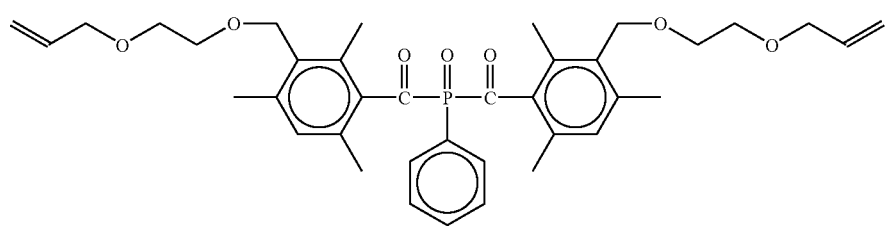

BAPOmAOEM

1st Stage: 3-(2-allyloxy-ethoxymethyl)-2,4,6-trimethyl-benzoic acid (AOEMB)

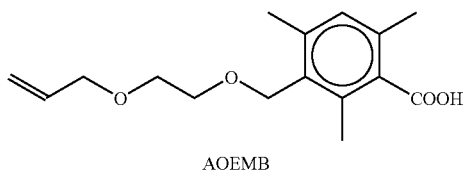

AOEMB 6.70 g (32 mmol) 3-chloromethane-2,4,6-trimethylbenzoic acid and 5.65 (101 mmol) KOH were introduced first under nitrogen atmosphere. 50 ml (468 mmol) 2-allyloxyethanol were added by syringe and the reaction started accompanied by stirring by heating to 70° C. The reaction was monitored by thin-layer chromatography, complete conversion being detected after 30 min. The reaction mixture was then transferred into a separating funnel and set to pH 1 with 2N hydrochloric acid. The product was extracted with ethyl acetate (EE) (3×75 ml) and the combined organic phases dried with anhydrous sodium sulphate. After removing the solvent in the rotary evaporator an oily liquid remained. Residual 2-allyloxyethanol was separated off by means of distillation (1 mbar, 75° C.) and the remaining oil cleaned by repeated digestion with hexane. After concentration the combined extracts produced 7.73 g (87% yield) of AOEMB as a colourless, waxy solid.

$^1$H-NMR (CDC$_3$): δ (ppm): 10.28 (s, 1H, —COOH), 6.90 (s, 1H, Ar—H$^5$), 5.98-5.82 (m, 1H, =CH—), 5.22-5.20 (dd, 2H, H$_2$C=), 4.60 (s, 2H, —CH$_2$—O—), 4.04-4.01 (d, 2H, —CH$_2$—O—), 3.65-3.63 (d, 4H, 2x —CH$_2$—O—), 2.43-2.34 (s, 9H, 3x —CH$_3$)

2nd Stage: 3-(2-allyloxy-ethoxymethyl)-2,4,6-trimethyl-benzoylchloride (AOEMBCl)

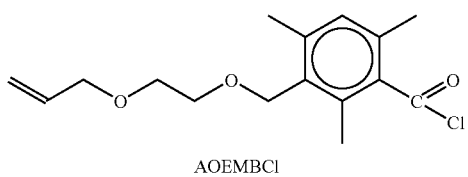

AOEMBCl 7.73 g (0.0278 mol) AOEMB was introduced into a flask, rinsed with argon, which was sealed with a septum. 77 ml toluene and 5 drops DMF were then added by syringe. The reaction was started by slow dropwise adding of 11.8 ml oxalic acid dichloride (foaming). The reaction was complete after 30 min. The precipitated by-products were separated under argon via a reverse frit, and finally solvent and surplus oxalic acid dichloride were drawn off in the rotary evaporator. After drying under high vacuum 7.15 g (87% yield) of AOEMB was obtained as a yellow oily residue.

$^1$H-NMR: (CDCl$_3$): δ (ppm): 6.91 (s, 1H, Ar—H$^5$), 5.90-5.84 (m, 1H, =CH—), 5.32-5.15 (dd, 2H, CH$_2$=), 4.57 (s, 2H, —CH$_2$—O—), 4.03-4.00 (d, 2H, —CH$_2$—O—), 3.66-3.64 (s, 4H, 2x —CH$_2$—O—), 2.43-2.33 (s, 9H, —CH$_3$).

3rd stage: bis-{3-[2-(2-allyloxy-ethoxymethyl]-2,4,6-trimethylbenzoyl}-phenylphosphine oxide (BAPOmAOEM)

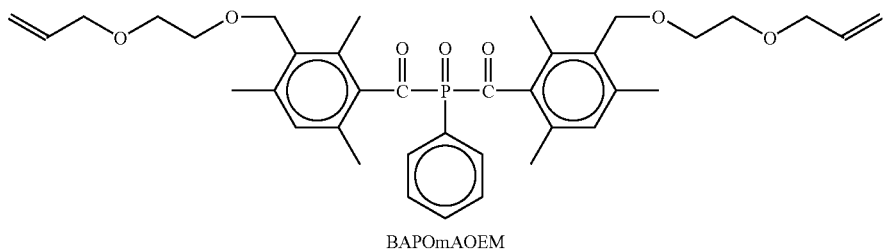

BAPOmAOEM 0.67 g (96.0 mmol) elemental lithium was weighed directly into a flask with argon and a small stirring rod. The flask was sealed by means of a septum and 32 ml dry THF was added to it via a syringe. A spatula tip of naphthalene was dissolved in some THF and also added dropwise. The mixture was then intensively stirred for 10 min and finally 2.88 g (16.0 mmol) P,P-dichlorophenylphosphine dissolved in 6 ml THF slowly added dropwise accompanied by intensive stirring. Cooling was carried out by means of a water bath because of the great exothermia of the reaction. In order to remove the non-reacted lithium the black solution was transferred into a dry argon-rinsed flask and 7.15 g (24.0 mmol) of the acid chloride AOEMBCl dissolved in 15 ml dry THF was slowly added dropwise to this accompanied by intensive stirring. After the end of the addition stirring was continued for a further hour and the solvent was then removed in the rotary evaporator. The residue was taken up in 20 ml toluene and oxidized by slow dropwise addition of 1.56 g (16.0 mmol) hydrogen peroxide solution (35%) accompanied by intensive stirring, the reaction mixture heating up strongly (cooling in the water bath). After 20 min the reaction mixture was taken up in 300 ml EE. The organic phase was washed with saturated sodium hydrogen carbonate solution (2×50 ml). The aqueous phase was re-extracted with EE (2×50 ml), the combined organic phases extracted with saturated common salt solution (brine) and dried after its separation with anhydrous sodium sulphate. The purification of the crude product took place by means of column chromatography, petroleum ether (PE): ethyl acetate (EE)=1:1 being used as solvent system. 1.9 g (24% yield) of BAPOmBAEO resulted as a viscous yellow oil.

$^1$H-NMR: (CDCl$_3$): δ (ppm): 7.81-7.86 (m, 2H, Ar—H), 7.38-7.51 (m, 3H, Ar—H), 6.83 (s, 2H, Ar—H), 5.78-5.97 (m, 2H, 2x =CH—), 5.12-5.28 (m, 4H, 2x CH$_2$=), 4.48 (s, 4H, 2x Ar—CH$_2$—O—), 3.96-3.99 (d, 4H, 2x =CH—C H₂—O—), 3.53 (bs, 8H, 4x —CH₂—O—), 2.33 (s, 6H, 2x Ar—CH₃), 2.17 (s, 6H, 2x Ar—CH₃), 2.08 (s, 6H, 2x Ar—CH₃).

Example 2

Preparation and Examination of Dental Materials Based on the Bisphenylphosphine Oxides from Example 1

To examine the photoinitiator activity and the storage stability of the photoinitiators in formulations a composition with the following components was prepared. It is a composition used as a dental primer for enamels and dentine.
(i) 22 wt.-% of the hydrolysis-stable cross-linker N,N'-diethyl-1,3-bis(acrylamido)-propane (DEBAMP);
(ii) 45 wt.-% of the acid monomer 2-[4-(dihydroxyphosphoryl)-2-oxa-butyl]-acrylic acid ethyl ester (DHPAE) and
(iii) 33 wt.-% water

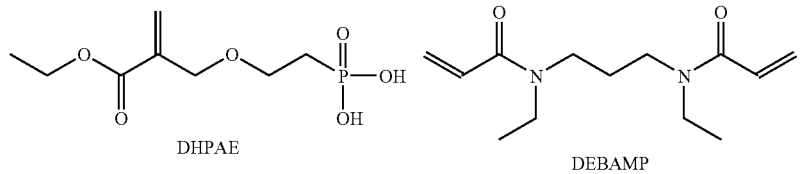

To prepare the model formulation, 0.022 mmol of the photoinitiator described in Example 1 were weighed into an analysis tube and made up to 1.00 g with the above composition and dissolved accompanied by slight heating. The activity of the molar concentration used of the photoinitiator approximately corresponded to the activity of a 0.8 wt.-% solution of camphorquinone/p-dimethylaminobenzoic acid ethyl ester (CC/DMAB), a photoinitiator system widely used in the dental sector.

Finally, for DSC measurements approx. 10 mg of the. initiator-containing composition was weighed into a small DSC dish made of aluminium and this small dish placed onto the right-hand sensor of the measurement cell of a DSC apparatus (DSC-50, Shimadzu). An empty small dish on the left-hand sensor served as reference. Recording from the DSC apparatus was started 2.0 min after the fitting of the small dish and irradiation started after 1.0 min had elapsed. A dental lamp with a wavelength of λ=400-500 nm (Astralis 3, Ivoclar Vivadent), intended for dental use, served as radiation source. The distance from the light source to the sample was 32 mm for all measurements. Once the DSC line was constant, the measurement was stopped. All measurements were carried out under air. A first measurement was carried out immediately after the preparation of the compositions, a second measurement after 60 days' storage of the compositions in the dark at 42° C. A mixture of camphorquinone and p-dimethylaminobenzoic acid and of the initiator [bis-(2,4,6-trimethylbenzoyl)-phenylphosphine oxide] (Irgacure 819, Ciba-Speciality Chemicals) customary in the trade were also examined as comparative initiators.

The time of the maximum heat flow $t_{max}$ (corresponds to the time taken to reach the highest polymerization rate in [s]), the area of the peak ΔH (corresponds to the released quantity of heat of polymerization in [J/g]) and the height of the peak h in [mW/mg] was specified in the result of the DSC measurement. The double-bond conversion (DBC) can be calculated via the area of the peak ΔH, the molecular weights MW of the monomers and the theoretical heats of polymerization known from the literature of the individual components of the compositions ΔH₀, which are listed in the following Table 1.

A theoretical quantity of heat of polymerization of the composition $\Delta H_{primer}$ of 207 J/g composition results for a complete double-bond conversion (DBC=100%). The double-bond conversion of the individual measurement can thus be calculated according to the following equation (A):

$$DBC[\%] = \frac{\Delta H}{\Delta H_{primer}} \cdot 100 \quad (A)$$

TABLE 1

Characteristics of the components of the compositions

| Component | MW[1] [g/mol] | ΔH₀[2] [J/mol] | Proportion [%] in the Composition |
|---|---|---|---|
| DHPAE[3] | 238 | 62,900 | 40 |
| DEBAMP[4] | 238 | 120,600 | 20 |
| Water | 18 | 0 | 40 |

[1]Molecular weight
[2]Theoretical heat of polymerization
[3]2-[4-(dihydroxyphosphoryl)-2-oxa-butyl]-acrylic acid ethyl ester
[4]N,N'-diethyl-1,3-bis(acrylamido)-propane The following general formula (B) can be produced for any other formulations:

$$DBC[\%] = \frac{\Delta H}{\sum_{x=1}^{n} \frac{\Delta H_0 \cdot w}{MW}} \cdot 100 \quad (B)$$

ΔH Heat of polymerization [J/g] (peak area)
ΔH₀ Theoretical heat of polymerization of the individual component [J/mol]
w Proportion by weight The polymerization rate $R_p$ can be calculated as follows from the height of the peak, the theoretical heat of polymerization and the density of the resin ρ (formula C):

$$R_P = \frac{h \times \rho}{\Delta H_{0P}} \quad (C)$$

$R_p$ Polymerization rate [mol l$^{-1}$s$^{-1}$]
h Height of the peak [mW/mg]
ρ Density of the resin [$ρ_{primer}$=1124 g/l]

The results of these calculations are shown in Table 2. These prove that the bisacylphosphine oxide BAPOmAOEM according to the invention shows a better reactivity vis-à-vis the compound Irgacure 819 after storage for 60 days at 42° C. In addition to its better solubility the initiator according to the invention is thus also characterized by a higher reactivity and a higher stability. A major advantage is that the double-bond conversion remains constant during storage. A higher double-bond conversion shows an extensive binding of the initiator into the polymer network. This is tantamount to a small quantity of initiator, that has not been bound in and can thus be eluted, which is advantageous from the viewpoint of biocompatibility.

TABLE 2

Results of the photo-DSC measurements

| Initiator | Storage time: 0 days | | | 60 days | | |
|---|---|---|---|---|---|---|
| | $t_{max}^1$ [s] | $R_p^2$ [mol/L s] | DBC$^3$ [%] | $t_{max}^1$ [s] | $R_p^2$ [mol/L s] | DBC$^3$ [%] |
| CC/DMAB$^{4,*}$ | 108 | 0.07 | 30 | — | — | — |
| Irgacure819$^{5,*}$ | 26 | 0.60 | 66 | 29 | 0.52 | 58 |
| BAPOmAOEM (Ex. 1) | 17 | 0.75 | 77 | 23 | 0.65 | 76 |

*Comparison example
$^1$Time of heat flow maximum
$^2$Polymerization rate according to Formula (C)
$^3$Double-bond conversion according to Formula (A)
$^4$Camphorquinone/p-dimethylaminobenzoic acid
$^5$Irgacure 819 was used due to its low solubility in a concentration of 0.005 mmol/g (= maximum solubility)

The invention claimed is:

1. Polymerizable dental material comprising at least one radically polymerizable monomer and at least one bisacylphosphine oxide of the Formula I,

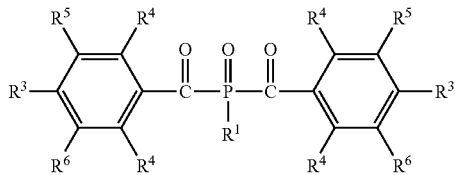

Formula (I)

in which the variables have the following meanings independently of one another:
R$^1$ a linear or branched C$_2$ to C$_{14}$ alkyl residue which can be interrupted by one or more O atoms, PG-Y—R$^2$—X—, or a substituted or unsubstituted aromatic C$_6$ to C$_{14}$ radical;
R$^2$ —[CH$_2$]$_n$—[—O—CH$_2$—CH$_2$]$_m$— with n=1, 2, 3, or 4 and m=0, 1, 2, or 3;
R$^3$ H, a linear or branched C$_1$ to C$_6$ alkyl residue or PG-Y—R$^2$—X—,
R$^4$ a linear or branched C$_1$-C$_6$ alkyl or —O—C$_1$-C$_6$ alkyl residue,
R$^5$ H or PG-Y—R$^2$—X—,
R$^6$ H or PG-Y—R$^2$—X—,
PG a polymerizable group,
X is absent, O or S,
Y is absent, O, S, an ester, amide or urethane group, the bisacylphosphine oxide having at least one PG-Y—R$^2$—X-group and Y being O if m is 0.

2. Dental material according to claim 1 in which R$^1$ is an aromatic C$_6$ to C$_{14}$ radical which is unsubstituted or substituted by one or more C$_1$ to C$_{15}$ alkoxy radicals and/or one or more PG-Y—R$^2$—X— groups.

3. Dental material according to claim 1 in which the one or more polymerizable groups are selected independently of one another from vinyl, allyl, (meth)acryloyl and/or vinylcyclopropyl.

4. Dental material according to claim 1 in which at least one of the variables has one of the following meanings:
R$^1$ phenyl which is unsubstituted or substituted by PG-Y—R$^2$—X—;
R$^3$ H, C$_1$-C$_3$ alkyl or PG-Y—R$^2$—X—;
R$^4$ C$_1$-C$_3$ alkyl or —O—C$_1$-C$_3$ alkyl;
R$^5$ H or PG-Y—R$^2$—X—;
R$^6$ H or PG-Y—R$^2$—X—;
PG —CH$_2$—CH=CH$_2$ or —CH=CH$_2$;
X is absent;
Y is absent or O.

5. Dental material according to claim 1 in which the bisacylphosphine oxide contains 1 to 5 PG-Y—R$^2$—X— groups.

6. Dental material according to claim 1 wherein the at least one radically polymerizable monomer comprises monofunctional (meth)acrylates, 2-(alkoxymethyl)acrylic acids, N-mono- or disubstituted acrylamides, N-mono-substituted methacrylamides, cross-linking (meth)acrylates, urethane reaction products of 2-(hydroxymethyl) acrylic acid and diisocyanates, ethylenically unsaturated pyrrolidones, bisacrylamides, or bis-(meth)acrylamides.

7. Dental material according to claim 1 wherein the at least one radically polymerizable monomer comprises radically polymerizable carboxylic acids, radically-polymerizable phosphonic acid monomers, radically polymerizable phosphoric acid esters, or radically polymerizable sulphonic acids.

8. Dental material according to claim 1 which contains at least one radically-polymerizable monomer which has one or more phosphonic acid groups or one or more phosphate groups, wherein these groups are present in the acid form or in partly esterified form.

9. Dental material according to claim 1 which contains at least one filler.

10. Dental material according to claim 9 wherein the at least one filler comprises inorganic particulate fillers; amorphous spherical oxide materials; nanoparticulate fillers; microfine fillers; nanoparticulate Al$_2$O$_3$, Ta$_2$O$_5$, $Yb_2$O$_3$, ZrO$_2$, Ag, or TiO$_2$; mixed oxides of at least one of SiO$_2$, ZrO$_2$ and/or TiO$_2$; minifillers; or X-ray-opaque fillers.

11. Dental material according to claim 9 wherein the at least one filler comprises amorphous spherical oxide materials; pyrogenic silica; nanoparticulate Al$_2$O$_3$, Ta$_2$O$_5$, Yb$_2$O$_3$, ZrO$_2$, Ag, or TiO$_2$; mixed oxides of at least one of SiO$_2$, ZrO$_2$ and TiO$_2$; precipitated silica; quartz, glass ceramic, or glass powder each having an average particle size of 0.01 to 1 μm; ytterbium trifluoride; or nanoparticulate barium sulphate.

12. Dental material according to claim 1 which further comprises at least one additive selected from stabilizers, flavoring agents, microbiocidal active ingredients, fluoride-ion releasing additives, optical brighteners, plasticizers or UV absorbers.

13. Dental material according to claim 1 which contains
a) 0.001 to 5 wt.-% bisacylphosphine oxide of the formula (I),
b) 5 to 80 wt.-% radically-polymerizable monomer, c) 1 to 60 wt.-% acid radically-polymerizable monomer,
d) 0 to 80 wt.-% solvent,
e) 0 to 85 wt.-% filler.

14. An adhesive dental material according to claim 13, which contains 0 to 30 wt.-% filler.

15. A cement or filling dental material according to claim 13, which contains 20 to 85 wt.-% filler.

16. Dental material according to claim 1 wherein the at least one radically polymerizable monomer comprises methyl, ethyl, butyl, benzyl, furfuryl, or phenyl(meth)acrylate; 2-hydroxyetheyl or propyl(meth)acrylate; mesityl methacrylate; 2-(ethoxymethyl)acrylic acid; 2-hydroxymetheylacrylic acid; N-ethyl acrylamide; N,N-dimethacrylamide, N-(2-hydroxyethyl)acrylamide; N-methyl-N-(2-hydroxyethyl)acrylamide; N-ethyl methacrylamide or N-(2-hydroxyethyl)methacrylamide; N-vinylpyrrolidones; allyl ethers; bisphenol-A-di(meth)acrylate; an addition product of methacrylic acid and bisphenol-A-diglycidylether(bis-GMA); an addition product of 2-hydroxyethyl methacrylate and 2,2,4-trimethylhexamethylene diisocyanate (UDMA); di-; tri- or tetraethylene glycoldi(meth)acrylate; trimethylolpropane tri(meth)acrylate; pentaerythritol tetra(meth)acrylate; butanediol di(meth)acrylate; 1,10-decanediol di(meth)acrylate or 1,12-dodecanediol di(meth)acrylate; urethane reaction product of 2-(hydroxymethyl)acrylic acid and 2,2,4-trimethylhexamethylene diisocyanate; urethane reaction product of 2-(hydroxymethyl)acrylic acid and isophorone diisocyanate; 1,6-bis(3-vinyl-2-pyrrolidonyl)-hexane; methylene bisacrylamide; ethylene bisacrylamide; N,N'-diethyl-1,3-bis-(acrylamido)-propane; 1,3-bis-(methacrylamido)-propane; 1,4-bis-(acrylamido)-butane; or 1,4-bis(acryloyl)-piperazine.

17. Dental material according to claim 1 wherein the at least one radically polymerizable monomer comprises maleic acid, acrylic acid, methacrylic acid, 2-(hydroxymethyl) acrylic acid, 4-(meth)acryloyloxyethyl trimellitic acid anhydride, 10-methacryloyloxydecyl malonic acid, N-(2-hydroxy-3-methacryloyloxypropyl)-N-phenylglycine, 4-vinylbenzoic acid; alkene phosphonic acids, vinyl phosphonic acid, 4-vinylphenylphosphonic acid, 4-vinylbenzylphosphonic acid, 2-methacryloyloxyethylphosphonic acid, 2-methacrylamidoethylphosphonic acid, 4-methacrylamido-4-methyl-pentyl-phosphonic acid, 2-[4-(dihydroxyphosphoryl)-2-oxa-butyl]-acrylic acid, 2-[2-dihydroxyphoshoyl)-ethoxymethyl]-acrylic acid-2,4,6-trimethyl-phenyl ester; 2-methacryloyloxypropylmonohydrogen phosphate, 2-methacryloyloxypropyldihydrogen phosphate, 2-methacryloyloxyethylmono hydrogen phosphate, 2-methacryloyloxyethyldihydrogen phosphate, 2-methacryloyloxyethylphenyl-hydrogen phosphate, dipentaerythritol-pentamethacryloyloxyphosphate, 10-methacryloyloxydecyl-dihydrogen phosphate, dipentaerythritolpentamethacryloyloxyphosphate, phosphoric acid mono-(1-acryloyl-piperidine-4-yl)-ester, 6-(methacrylamido)hexyldihydrogen phosphate and 1,3-bis-(N-acryloyl-N-propyl-amino)propane-2-yl-dihydrogen phosphate; vinyl sulphonic acid, 4-vinylphenyl sulphonic acid or 3-(methacrylamido)propyl sulphonic acid.

18. Dental material according to claim 1 in which $R^1$ is phenyl which is unsubstituted or substituted by PG-Y—$R^2$—X—.

* * * * *